(12) United States Patent
Sugo et al.

(10) Patent No.: US 9,591,976 B2
(45) Date of Patent: Mar. 14, 2017

(54) METHOD AND APPARATUS FOR MEASURING BLOOD VOLUME

(71) Applicant: NIHON KOHDEN CORPORATION, Tokyo (JP)

(72) Inventors: Yoshihiro Sugo, Tokyo (JP); Tomoyuki Sakai, Tokyo (JP); Mami Terao, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 492 days.

(21) Appl. No.: 14/059,579

(22) Filed: Oct. 22, 2013

(65) Prior Publication Data

US 2014/0121544 A1 May 1, 2014

(30) Foreign Application Priority Data

Oct. 30, 2012 (JP) .................... 2012-239369

(51) Int. Cl.
| | |
|---|---|
| *A61B 5/0205* | (2006.01) |
| *A61B 5/029* | (2006.01) |
| *A61B 5/021* | (2006.01) |
| *A61B 5/08* | (2006.01) |
| *A61B 5/0215* | (2006.01) |
| *A61B 5/022* | (2006.01) |

(52) U.S. Cl.
CPC ............ *A61B 5/029* (2013.01); *A61B 5/0205* (2013.01); *A61B 5/02108* (2013.01); *A61B 5/02125* (2013.01); *A61B 5/0816* (2013.01); *A61B 5/022* (2013.01); *A61B 5/0215* (2013.01)

(58) Field of Classification Search
CPC .............. A61B 5/0205; A61B 5/02108; A61B 5/02125; A61B 5/029; A61B 5/0816
See application file for complete search history.

(56) References Cited

U.S. PATENT DOCUMENTS

| | | | |
|---|---|---|---|
| 6,547,740 B2 | 4/2003 | Sugo et al. | |
| 6,652,466 B2 | 11/2003 | Sugo et al. | |
| 7,615,011 B2 | 11/2009 | Sugo et al. | |
| 2002/0151805 A1 | 10/2002 | Sugo et al. | |
| 2005/0124903 A1 | 6/2005 | Roteliuk et al. | |
| 2005/0124904 A1 | 6/2005 | Roteliuk | |
| 2005/0187481 A1 | 8/2005 | Hatib et al. | |

(Continued)

FOREIGN PATENT DOCUMENTS

| | | |
|---|---|---|
| CN | 101176663 A | 5/2008 |
| CN | 101489472 A | 7/2009 |

(Continued)

OTHER PUBLICATIONS

Westphal et al, Pulse Pressure Respiratory Variation as an Early Marker of Cardiac Output Fall in Experimental Hemorrhagic Shock, 2007, Artificial Organs, 31(4):284-289.*

(Continued)

*Primary Examiner* — Jacqueline Cheng
*Assistant Examiner* — Angeline Premraj
(74) *Attorney, Agent, or Firm* — Sughrue Mion, PLLC (57) ABSTRACT

Method for measuring a blood volume is provided. At least two types of respiratory variation data; for instance, data pertinent to respiratory variations in stroke volume (SVV) data, data pertinent to respiratory variations in an amplitude of a pulse wave (PAV), a pulse wave transit time (PWTT) in a respiratory cycle, and a heart rate (HR) in a predetermined time, are measured, and patient's inherent coefficients α, β, and K are calculated, whereby a cardiac output can be determined by an equation CO=K (α*PWTT+β)*HR.

6 Claims, 4 Drawing Sheets

(56) References Cited

U.S. PATENT DOCUMENTS

| | | | |
|---|---|---|---|
| 2005/0222514 A1* | 10/2005 | Sugo | A61B 5/029 600/526 |
| 2007/0149884 A1 | 6/2007 | Roteliuk et al. | |
| 2007/0167852 A1 | 7/2007 | Sugo et al. | |
| 2008/0015451 A1 | 1/2008 | Hatib et al. | |
| 2008/0033305 A1 | 2/2008 | Hatib et al. | |
| 2008/0300494 A1 | 12/2008 | Hatib et al. | |
| 2009/0062666 A1 | 3/2009 | Roteliuk | |
| 2010/0268101 A1 | 10/2010 | Sugo | |
| 2010/0268518 A1 | 10/2010 | Sugo | |
| 2011/0275943 A1 | 11/2011 | Roteliuk | |
| 2012/0150003 A1 | 6/2012 | Zhang | |
| 2014/0213914 A1 | 7/2014 | Roteliuk | |
| 2015/0065828 A1 | 3/2015 | Al Hatib et al. | |

FOREIGN PATENT DOCUMENTS

| | | |
|---|---|---|
| CN | 101766481 A | 7/2010 |
| EP | 2292143 A1 | 3/2011 |
| JP | 2005-312947 A | 11/2005 |
| JP | 2008-506472 A | 3/2008 |
| JP | 2010-264228 A | 11/2010 |
| JP | 4742644 B2 | 5/2011 |

OTHER PUBLICATIONS

Communication dated Sep. 6, 2015 issued by the State Intellectual Property Office of P.R. China in counterpart Chinese Patent Application No. 201310504855.3.

European Search Report dated Feb. 7, 2014 issued by the European Patent Office in counterpart European Patent Application No. 13189096.4.

Office Action dated Jan. 26, 2016, issued by the Japanese Patent Office in counterpart Japanese Application No. 2012-239369.

Chest, Stroke Volume and Pulse Pressure Variation for Prediction of Fluid Responsiveness in Patients Undergoing Off-Pump Coronary Artery Bypass Grafting, 2005, 128, 848-854.

* cited by examiner

*FIG. 4A*
ELECTROCARDIOGRAM

*FIG. 4B*
WAVEFORM OF AORTIC PULSE WAVE

*FIG. 4C*
WAVEFORM IN PERIPHERAL ARTERY

*FIG. 4D*
WAVEFORM OF PERIPHERAL PULSE AVE

METHOD AND APPARATUS FOR MEASURING BLOOD VOLUME

BACKGROUND

The presently disclosed subject matter relates to method and apparatus for measuring a blood volume ejected by heart pulsation.

Monitoring variations in hemodynamics of a patient in an operating room, an intensive care unit, an emergency treatment room, or a dialysis treatment room within a healthcare center must be performed continuously with minimum possible interruption. Such monitoring of variations in hemodynamics of the patient has hitherto been practiced primarily by means of directly monitoring blood pressure.

A living body, however, usually controls a cardiac output and vascular resistance such that a blood pressure of a nerve center falls within a certain range. Consequently, in order to ascertain variations in hemodynamics of the patient at an early stage, only direct monitoring of a blood pressure is not sufficient. Further, when a change in blood pressure occurs, a cause of the change must be ascertained. For these reasons, in addition to monitoring blood pressure, monitoring a cardiac output is necessary. A known method for measuring a cardiac output includes a thermodilution method, a die dilution method, and an ultrasonic method.

Incidentally, any of the methods described above cannot be readily performed without interruption in light of requirements for sophisticated skills of a healthcare worker and a high degree of invasion of a patient. Under the methods, it has been difficult to continuously monitor variations in hemodynamics of the patient at all times.

On the contrary, Japanese Patent No. 4742644 discloses a blood volume measurement method that enables noninvasive, continuously monitoring of variations in hemodynamics of the patient without interruption, that obviates a necessity for sophisticated skills of a healthcare worker, such as insertion of a catheter, and that assuages a patient's pain. According to the blood volume measurement method, a cardiac output is calculated by utilization of a correlation between a pulse wave transit time and a stroke volume.

However, under the blood volume measurement method described in Japanese Patent No. 4742644, blood pressure must be measured at least twice or more on the occasion of determination of a coefficient $\alpha$ inherent in the patient, which results in an increase in measurement time and may impose unwanted stress on the patient. Further, when a difference does not exist between two or more measured values of blood pressure, calibration of $\alpha 0$ and $\beta$ cannot be practiced. For this reason, blood pressure must be measured while the patient is put under load in order to make values of blood pressure differ from each other; hence, measuring values of blood pressure itself is not easy.

SUMMARY

This presently disclosed subject matter provides a blood volume measurement method and a blood volume measurement apparatus that do not require a long time in performing measurement; that are simple; and that can assuage stress on a patient.

It is therefore an aspect of the presently disclosed subject matter to provide a blood volume measurement method for calculating a cardiac output (CO) from a pulse wave transit time, the method comprising the steps of:

measuring respiratory variations of at least two types of parameters;

measuring a pulse wave transit time (PWTT) in a respiratory cycle;

measuring a heart rate (HR) in a predetermined time; and calculating a cardiac output (CO) by use of the respiratory variations of at least the two types of parameters, the pulse wave transit time, and the heart rate.

The respiratory variations of at least the two types of parameters may include respiratory variations in stroke volume (SVV) and respiratory variations in an amplitude of a pulse wave (PAV).

Patient's inherent coefficients $\alpha$, $\beta$, and K may be calculated by use of the respiratory variations of at least the two types of parameters and the pulse wave transit time, and the cardiac output is determined by an equation $$CO=K(\alpha*PWTT+\beta)*HR.$$

The patient's inherent coefficient $\alpha$ may be determined by an equation $$\alpha=-(PAV*PP1)/(PAV*(PWTTavg-PWTT1)+PWTTmax-PWTTmin), \text{ where}$$

PP1 is actually measured pulse pressure; PWTTavg is an average pulse wave transit time in a respiratory cycle; PWTT1 is an actually measured pulse wave transit time; PWTTmax is a maximum value of pulse wave transit time in the respiratory cycle; and PWTTmin is a minimum value of pulse wave transit time in the respiratory cycle.

The respiratory variations of at least the two types of parameters may include respiratory variations in stroke volume (SVV) and respiratory variations in pulse pressure (PPV).

It is another aspect of the presently disclosed subject matter to provide a blood volume measurement apparatus that calculates a cardiac output (CO) from a pulse wave transit time, comprising:

a respiratory variation measurement unit configured to measure respiratory variations of at least two types of parameters;

a pulse wave transit time measurement unit configured to measure a pulse wave transit time (PWTT) in a respiratory cycle;

a heart rate calculation unit configured to measure and calculate a heart rate (HR) in a predetermined time; and a cardiac output calculation unit configured to calculate a cardiac output (CO) with use of the respiratory variations of at least the two types of parameters, the pulse wave transit time, and the heart rate.

DETAILED DESCRIPTION OF EMBODIMENTS

An embodiment of a blood volume measurement method and a measurement apparatus of the presently disclosed subject matter is hereunder described by reference to the accompanying drawings.

First, explanations are hereunder given to a principle in measuring a volume of blood (a cardiac output: CO) ejected by heart pulsation.

According to a Windkessel model that is an index to diagnosis of a blood vessel, a flow volume (SV−Qs) determined by subtracting a efflux flow volume to a periphery during systole of the heart (Qs) from a volume of blood flowed into an aorta during the systole of the heart; that is, a stroke volume (SV), can be expressed as follows by use of aortic compliance (C), and pulse pressure [PP: a difference between systolic pressure (the maximum blood pressure) and diastolic pressure (the minimum blood pressure)].

$$SV-Qs=C*PP \quad (\text{Eq. 1})$$

A efflux flow volume to the periphery during the diastole of the heart (Qd) is equal to SV−Qs. Qs and Qd represent values acquired by dividing the systolic and diastolic arterial pressures V by the vascular resistance R and then multiplying by the systolic duration Ts and the diastolic duration Td, respectively. For simplicity, given that Qs is proportional to Ts and that Qd is also proportional to Td, they can be expressed as follows:

$$(Qd=)SV-Qs=SV*Td/(Ts+Td) \quad (\text{Eq. 2}).$$

From Equations 1 and 2, we have $$SV*Td/(Ts+Td)=C*PP$$

$$SV=C*PP*(1+Ts/Td) \quad (\text{Eq. 3})$$

Suppose $C*(1+Ts/Td)=K$ on condition that C and Ts/Td are constant during a measurement time, we have $$SV=K*PP \quad (\text{Eq. 4})$$

$$PP=SV*1/K \quad (\text{Eq. 5})$$

As above, according to the Windkessel model, pulse pressure PP becomes proportional to the stroke volume SV.

Pulse pressure PP1 that will be actually measured includes pulse pressure PP2 based on Eq. 5 (although reference symbol PP is employed in Eq. 5, PP2 is employed in the following descriptions) and an augmentation PP3 of pulse pressure observed upon administration, for instance, a vasoconstrictor, and is expressed as $$PP1=PP2+PP3 \quad (\text{Eq. 6}).$$

In a case where PP3 is not observed, Eq. 4 and Eq. 6 will give $$SV=K*PP1 \quad (\text{Eq. 7}).$$

Therefore, SV can be actually measured from actually measured blood pressure (pulse pressure PP1). However, since PP1 already includes PP3 in the administration of a vasoconstrictor, SV will be eventually overvalued. This has hitherto been a problem in calculating SV from blood pressure.

With regard to the accuracy in measurement of an apparatus which enables calculation of the stroke volume as well as the cardiac output from the waveform of the arterial pressure measured invasively, the following is reported: "For a patient admitted to the ICU (intensive care unit) after a surgery, when the vascular resistance changed by about 60% upon administration of a vasoconstrictor phenylephrine, a remarkably large bias was observed between the measurements by the apparatus described above and the measurements by the cardiac output computer operating in the thermodilution mode used as the standard method, the values of the former being greater than those of the latter. In that case, there is accordingly a need for re-calibration by the blood volume flowmeter operating in the thermodilution mode." Further, in the administration of a vasoconstrictor, it is known that, in the administration of a vasoconstrictor or the like, the pulse pressure increases by influence of a reflected wave from the periphery, and PP3 corresponds to this augmentation.

A pulse wave transit time (hereinafter, referred to as PWTT), which corresponds to a time taken until the reach from an R wave in an electrocardiogram to rise of an $SpO_2$ pulse wave of the periphery, includes the following component.

$$PWTT=PEP+PWTTa+PWTTb \quad (\text{Eq. 8})$$

FIGS. 4A to 4D are charts illustrating waveforms of respective pulse waves measured from the patient. As illustrated, PEP is the pre-ejection period of the heart, which is the duration from the initiation of electric stimulation of the heart to the opening of the aortic valve. PWTTa is a time taken for the pulse wave to be propagated from its generation in the aorta after the opening of the aortic valve to an artery at the periphery where typically blood pressure measurement is conducted invasively. PWTTb is a time taken for the pulse wave to be further propagated from the artery at the periphery to a peripheral blood vessel where photoplethysmogram is measured.

A duration of (PEP+PWTTa) from an R wave in the electrocardiogram (ECG) to a onset of rising a pulse wave at a femoral artery was measured by use of 10 adult dogs. A relationship between the duration of (PEP+PWTTa) and pulse pressure was measured under several conditions such as, administration of a vasoconstrictor, administration of the vasodilator, increase of a myocardial contractility, attenuation of myocardial contractility, and blood removal. In this way, it was found correlation between the pulse pressure PP1 and the duration of (PEP+PWTTa).

The relationship between the pulse pressure PP1 and PEP+PWTTa can be expressed as Eq. 9.

$$PEP+PWTTa=a*PP1+b \quad (\text{Eq. 9})$$

Further, the relationship between PWTTb and PP1 is expressed as Eq. 10.

$$PWTTb=c*PP1+d+e \quad (\text{Eq. 10})$$

Since it was discovered that, in a case where PP3 appears with the use of a vasoconstrictor, PWTTb tends to be prolonged as compared to cases under other conditions, a portion corresponding to this prolongation is represented by "e" (where, e is not limited to a constant).

Eq. 8 is then rewritten as follows according to Eq. 9 and Eq. 10.

$$PWTT=(a*PP1+b)+(c*PP1+d+e)$$

$$PP1=1/(a+c)*(PWTT-b-d-e) \quad (\text{Eq. 11})$$

A right side of Eq. 5 is substituted into PP2 of Eq. 6, whereby we have $$PP1=SV*1/K+PP3 \quad (\text{Eq. 12}).$$

Eq. 11 and Eq. 12 give $$1/(a+c)*PWTT-(b+d)/(a+c)=SV*1/K+PP3+e/(a+c)$$

$$SV=K*(1/(a+c)*PWTT-(b+d)/(a+c))- \\ K*(PP3+e/(a+c)) \quad (\text{Eq. 13}).$$

As mentioned above, it was experimentally found out that PWTTb tends to be prolonged when PP3 appears as a result of use of the vasoconstrictor. Administration of phenylephrine results in appearance of PP3, whereupon PP1 augments.

However, the relationship between PWTTb and PP1 which may be observed in cases of blood removal or administration of pentobarbital is no longer observed with the administration of phenylephrine, and PWTTb shows a tendency to be prolonged. Therefore, it has been experimentally discovered that there is maintained a negative correlation between SV and PWTT even upon administration of phenylephrine, which may be still observed under different conditions, and thus the second term (K(PP3+e/(a+c))) in the right side of Eq. 13 may be substantially ignored.

Accordingly, let $1/(a+c)=\alpha$ and $-(b+d)/(a+c)=\beta$, then $$SV = K^*(\alpha^*PWTT + \beta) \quad \text{(Eq. 14)},$$

where $\alpha$ and $\beta$ are patient's inherent coefficients to be experimentally determined.

From a relationship of SV=CO/HR, an estimated cardiac output esCO can be calculated by the following equation (HR: Heart Rate).

$$esCO = K^*(\alpha^*PWTT + \beta)^*HR \quad \text{(Eq. 15)}$$

where esCO is a cardiac output represented by L/min, and K is a patient's inherent constant to be experimentally determined.

In this regard, Eq. 15 can also be replaced as follows:

$$esCO = (\alpha K^*PWTT + \beta K)^*HR \quad \text{(Eq. 16)}$$

where $\alpha K$ and $\beta K$ are patient's inherent coefficients to be experimentally determined.

If SV and esCO are calculated by use of PWTT as in Eq. 14, Eq. 15, and Eq. 16, a correlation, such as that found under other conditions will still be maintained between SV and PWTT even when pulse pressure augments as in the case of use of a vasoconstrictor. Accordingly, a problem in the related art that occurs when SV is calculated by use of blood pressure can be solved. Therefore, CO is not overestimated.

Figure 1:
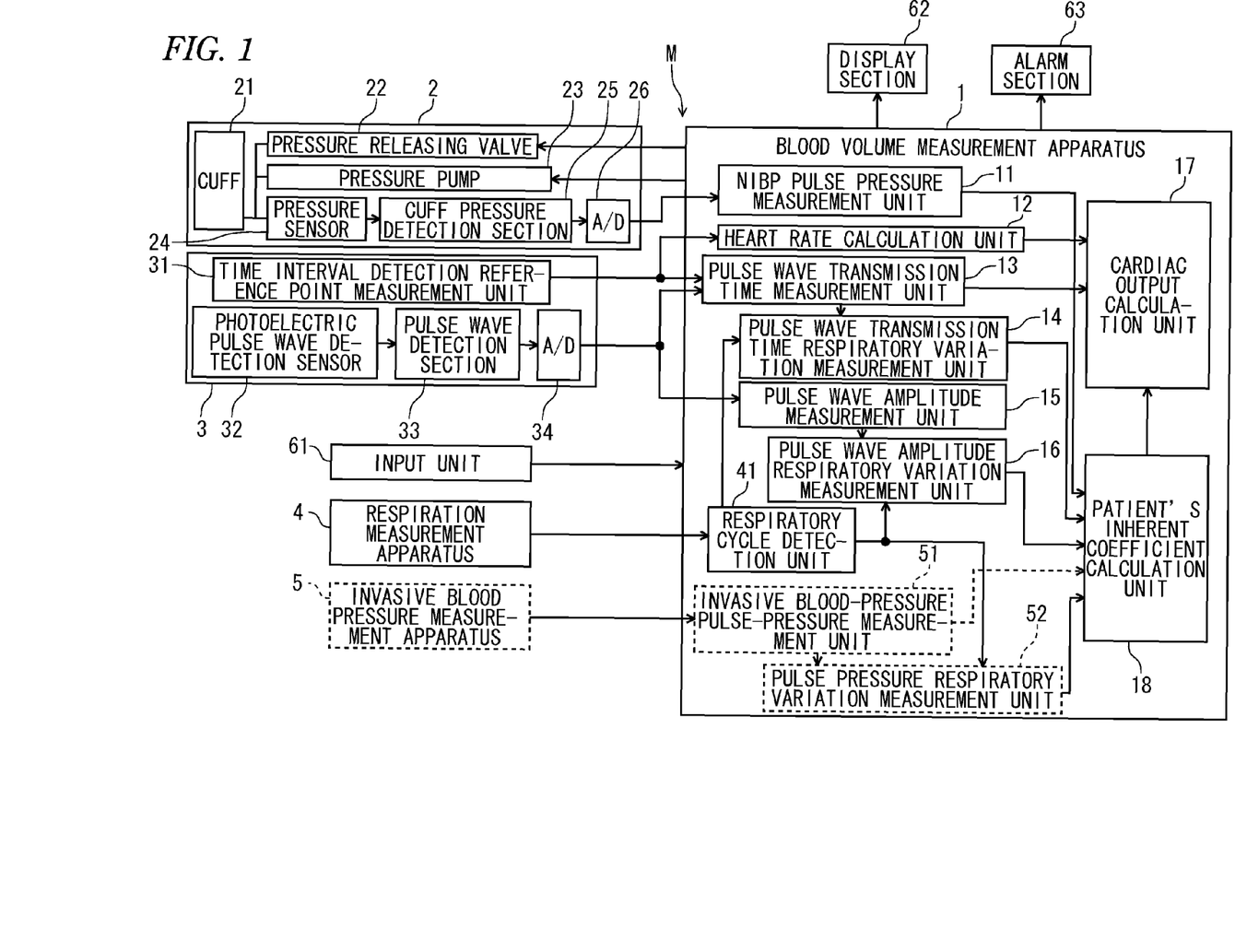
FIG. 1 is a block diagram illustrating a configuration of one mode of a patient monitor with a blood volume measurement apparatus of the presently disclosed subject matter.

FIG. 1 illustrates the patient monitor with a blood volume measurement apparatus of the presently disclosed subject matter. On the occasion of explanation, a reference is made, as necessary, to FIG. 2.

A patient monitor M has a blood volume measurement apparatus 1 that measures a volume of patient's blood; a systolic-pressure diastolic-pressure measurement apparatus 2 that measures systolic pressure and diastolic pressure of the heart; a PWTT detector 3 that detects an R wave in an electrocardiogram and a peripheral pulse wave; a respirometer 4; and an invasive blood pressure measurement apparatus 5.

The systolic-pressure diastolic-pressure measurement apparatus 2 is one that measures patient's blood pressure according to a non-invasive blood pressure measurement (NIBP) method and has a cuff 21, a pressure releasing valve 22, a pressure pump 23, a pressure sensor 24, a cuff pressure detection section 25, and an A-D converter 26.

Figure 2:
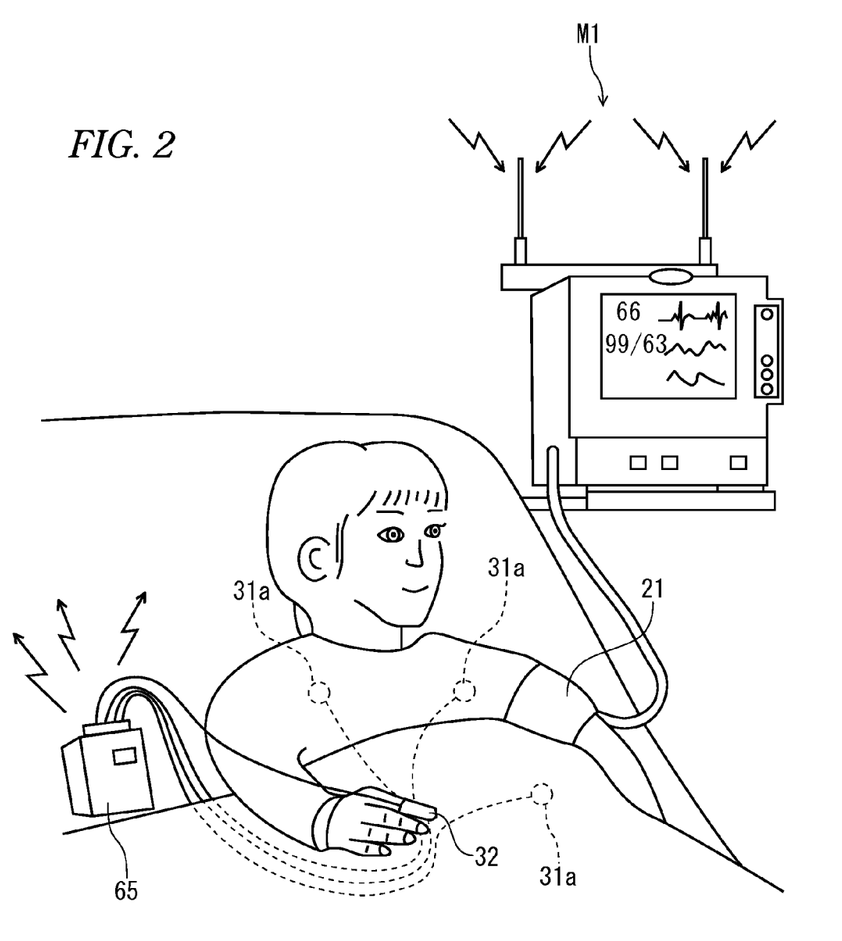
FIG. 2 illustrates an embodiment of measurement mode in which a patient is outfitted with electrocardiogram measurement unit and peripheral pulse wave detection unit.

Specifically, as shown in FIG. 2, the systolic-pressure diastolic-pressure measurement apparatus 2 measures blood pressure while the patient wears the cuff 21 around his/her upper arm.

An interior of the cuff 21 is opened or closed with respect to an atmosphere as a result of opening/closing of the pressure releasing valve 22. The pressure releasing valve 22 is opened or closed in accordance with a control signal output from the blood volume measurement apparatus 1. Moreover, the cuff 21 is supplied with air from the pressure pump 23. An air supply is controlled in accordance with a control signal output from the blood volume measurement apparatus 1.

The cuff 21 is also connected to the pressure sensor 24 (a cuff pulse wave sensor), and the cuff pressure detection section 25 detects an output from the sensor. An output from the cuff pressure detection section 25 is converted into a digital signal by means of the A-D converter 26, and the thus-converted digital signal is input to NIBP pulse pressure measurement unit 11 of the blood volume measurement apparatus 1.

The pressure releasing valve 22, the pressure pump 23, the pressure sensor 24, the cuff pressure detection section 25, and the A-D converter 26 are provided in a patient monitor main body (a bedside monitor) M1 of the patient monitor M.

The PWTT detector 3 may include interval detection reference point measurement unit 31, a photoelectric pulse wave detection sensor 32, a pulse wave detection section 33, and an A-D converter 34.

The time interval detection reference point measurement unit 31 measures a point of time when an R wave has occurred in an electrocardiogram as a time interval reference point. An output from the measurement unit 31 is converted into a digital signal by the A-D converter and input to heart rate calculation unit 12 and the PWTT measurement unit 13 of the blood volume measurement apparatus 1.

Figures 4A, 4B:
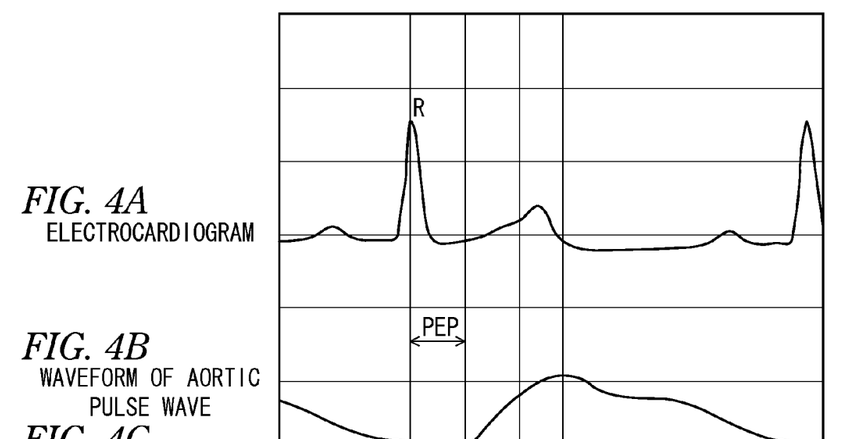
FIGS. 4A to 4D are charts illustrating a relationship among PEP, PWTTa, PWTTb, and PWTT.

To be specific, as shown in FIG. 2, the time interval detection reference point measurement unit 31 is made up of an electrocardiogram electrode 31a (electrocardiogram measurement unit) to be attached to a patient's chest. Data measured by the electrocardiogram electrode 31a are delivered, by wireless, to the patient monitor main body M1 from a measured data transmitter 65 electrically connected to the electrocardiogram electrode 31a. The transmitted measured data are converted into a digital signal by the A-D converter in the patient monitor main body M1 and input to the heart rate calculation unit 12 and the PWTT measurement unit 13. As a result, an electrocardiogram waveform, such as that shown in FIG. 4A, is generated.

As shown in FIG. 2, the photoelectric pulse wave detection sensor 32 is attached to a patient's peripheral portion, such as a finger, and measures; for instance, blood oxygen saturation ($SpO_2$), thereby determining a PWTT. The photoelectric pulse wave detection sensor 32 is electrically connected to the measured data transmitter 65, and the data measured by the sensor 32 are delivered, by wireless, to the patient monitor main body M1.

Figures 4C, 4D:
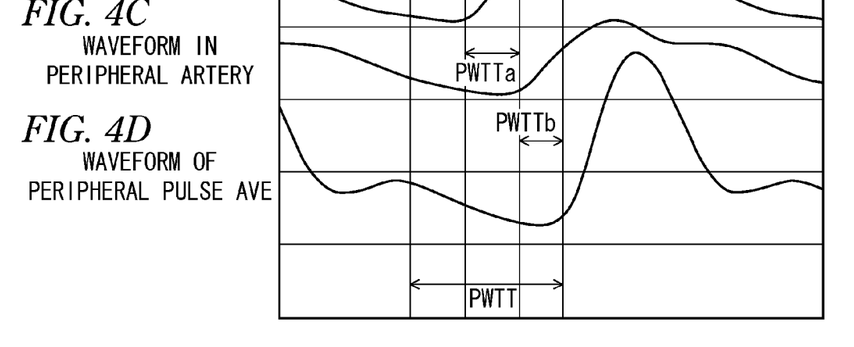

The measured data are delivered to the pulse wave detection section 33 in the patient monitor main body M1, whereby a pulse wave (a photoelectric pulse wave) of the patient's area where the photoelectric pulse wave detection sensor 32 is put is detected. An output from the pulse wave detection section 33 is converted into a digital signal by the A-D converter 34, and the digital signal is then input to the PWTT measurement unit 13 and pulse wave amplitude measurement unit 15 of the blood volume measurement apparatus 1. A waveform of the photoelectric pulse wave (i.e., a waveform of the periphery), such as that shown in FIG. 4D, is thus obtained.

The respirometer 4 continuously measures patient's respiration. Respiratory data measured by the respirometer 4 are input to respiratory cycle detection unit 41 of the blood volume measurement apparatus 1.

The invasive blood pressure measurement unit 5 measures blood pressure according to an invasive method (IBP: Invasive blood pressure) by inserting a catheter into a patient's blood vessel. Blood pressure data measured by the invasive blood pressure measurement apparatus 5 are input to invasive blood-pressure pulse-pressure measurement unit 51 of the blood volume measurement apparatus 1.

The blood volume measurement apparatus 1 is an apparatus that measures a cardiac output on the basis of respiratory variation data and may include NIBP pulse pressure measurement unit 11, the heart rate calculation unit 12, the PWTT measurement unit 13, PWTT respiratory variation measurement unit 14, the pulse wave amplitude measurement unit 15, pulse wave amplitude respiratory variation measurement unit 16, cardiac output calculation unit 17, patient's inherent coefficient calculation unit 18, respiratory cycle detection unit 41, the intrusive blood-pressure pulse-pressure measurement unit 51, and pulse pressure respiratory variation measurement unit 52. The blood volume measurement apparatus 1 is provided in the patient monitor main body M1 of the patient monitor M.

The NIBP pulse pressure measurement unit 11 measures NIBP pulse pressure according to blood pressure data measured by the systolic-pressure diastolic-pressure measurement apparatus 2. The NIBP pulse pressure is calculated from a difference between systolic (the maximum) pressure and diastolic (the minimum) pressure. The measured NIBP pulse pressure is input to the patient's inherent coefficient calculation unit 18.

The heart rate calculation unit 12 calculates the number of heart beats per minute (a heart rate) from a reference point (a point in time when an R wave has occurred) measured by the time interval detection reference point measurement unit 31. The calculated heart rate is input to the cardiac output calculation unit 17.

The PWTT measurement unit 13 measures a PWTT on the basis of the reference point (the point in time when an R wave has occurred) measured by the time interval detection reference point measurement unit 31 and a waveform of the periphery detected by the photoelectric pulse wave detection sensor 32. The measured PWTT is input to the cardiac output calculation unit 17 and the PWTT respiratory variation measurement unit 14. In this regard, as shown in FIGS. 4A to 4D, the PWTT is designated by a time difference from when the R wave has appeared in an electrocardiogram until when a peripheral pulse wave rises.

The PWTT respiratory variation measurement unit 14 measures respiratory variations occurred in the PWTT on the basis of the respiratory cycle detected by the respiratory cycle detection unit 41 as well as the PWTT by the PWTT measurement unit 13. The measured respiratory variations occurred within the PWTT are input to the patient's inherent coefficient calculation unit 18.

The pulse wave amplitude measurement unit 15 measures an amplitude of a pulse wave on the basis of the waveform of the periphery detected by the photoelectric pulse wave detection sensor 32. The measured amplitude of the pulse wave is input to the pulse wave amplitude respiratory variation measurement unit 16.

The pulse wave amplitude respiratory variation measurement unit 16 measures respiratory variations in an amplitude of the pulse wave (PAV: pulse amplitude variations) on the basis of the amplitude of the pulse wave measured by the pulse wave amplitude measurement unit 15 and the respiratory cycle detected by the respiratory cycle detection unit 41. The measured respiratory variations in the amplitude of the pulse wave are input to the patient's inherent coefficient calculation unit 18.

The respiratory cycle detection unit 41 detects a respiratory cycle from the respiratory data measured by the respirometer 4. The detected respiratory cycle is input to the PWTT respiratory variation measurement unit 14, the pulse wave amplitude respiratory variation measurement unit 16, and the pulse pressure respiratory variation measurement unit 52.

The invasive blood-pressure pulse-pressure measurement unit 51 measures IBP pulse pressure on the basis of the blood pressure data measured by the invasive blood pressure measurement apparatus 5. The measured IBP pulse pressure is input to the pulse pressure respiratory variation measurement unit 52. In this respect, there can also be adopted another configuration in which the IBP pulse pressure measured by the invasive blood-pressure measurement unit 5 is input directly to the patient's inherent coefficient calculation unit 18.

The pulse pressure respiratory variation measurement unit 52 measures respiratory variations in pulse pressure (PPV: pulse pressure variations) on the basis of the IBP pulse pressure measured by the invasive blood-pressure pulse-pressure measurement unit 51 and the respiratory cycle measured by the respiratory cycle detection unit 41. The measured respiratory variations in pulse pressure are input to the patient's inherent coefficient calculation unit 18.

The patient's inherent coefficient calculation unit 18 calculates a patient's inherent coefficient on the basis of the NIBP pulse pressure measured by the NIBP pulse pressure measurement unit 11, the respiratory variations that occurred in the PWTT and were measured by the PWTT respiratory variation measurement unit 14, and the respiratory variations in an amplitude of a pulse wave measured by the pulse wave amplitude respiratory variation measurement unit 16. The calculated coefficient is input to the cardiac output calculation unit 17. In this regard, the respiratory variations in pulse pressure measured by the pulse pressure respiratory variation measurement unit 52 can also be used in place of the PAV.

The cardiac output calculation unit 17 calculates a cardiac output from the heart rate calculated by the heart rate calculation unit 12, the PWTT measured by the PWTT measurement unit 13, and the coefficient calculated by the patient's inherent coefficient calculation unit 18.

Input unit 61 is connected to the blood volume measurement apparatus 1, and the healthcare worker inputs required data from the outside by way of the input unit 61. A display section 62 is connected to the blood volume measurement apparatus 1, and the measured biological information about the patient is displayed on the display section 62. Further, an alarm section 63 is connected to the blood volume measurement apparatus 1. If an abnormality in the measured biological information is detected, the alarm section 63 generates an alarm.

Explanations are now given to a blood volume measurement method for determining an estimated cardiac output (esCO) from Eq. 16; namely, esCO=($\alpha$K*PWTT+$\beta$K)*HR.

The patient's inherent coefficients $\alpha$, $\beta$, and K are determined with use of respiratory variations and by means of calibration, thereby calculating esCO. The coefficients $\alpha$ and $\beta$ are calibrated when an augmentation does not exist in pulse pressure (PP), which would otherwise be caused by administration of a vasoconstrictor, or the like.

Figure 3:
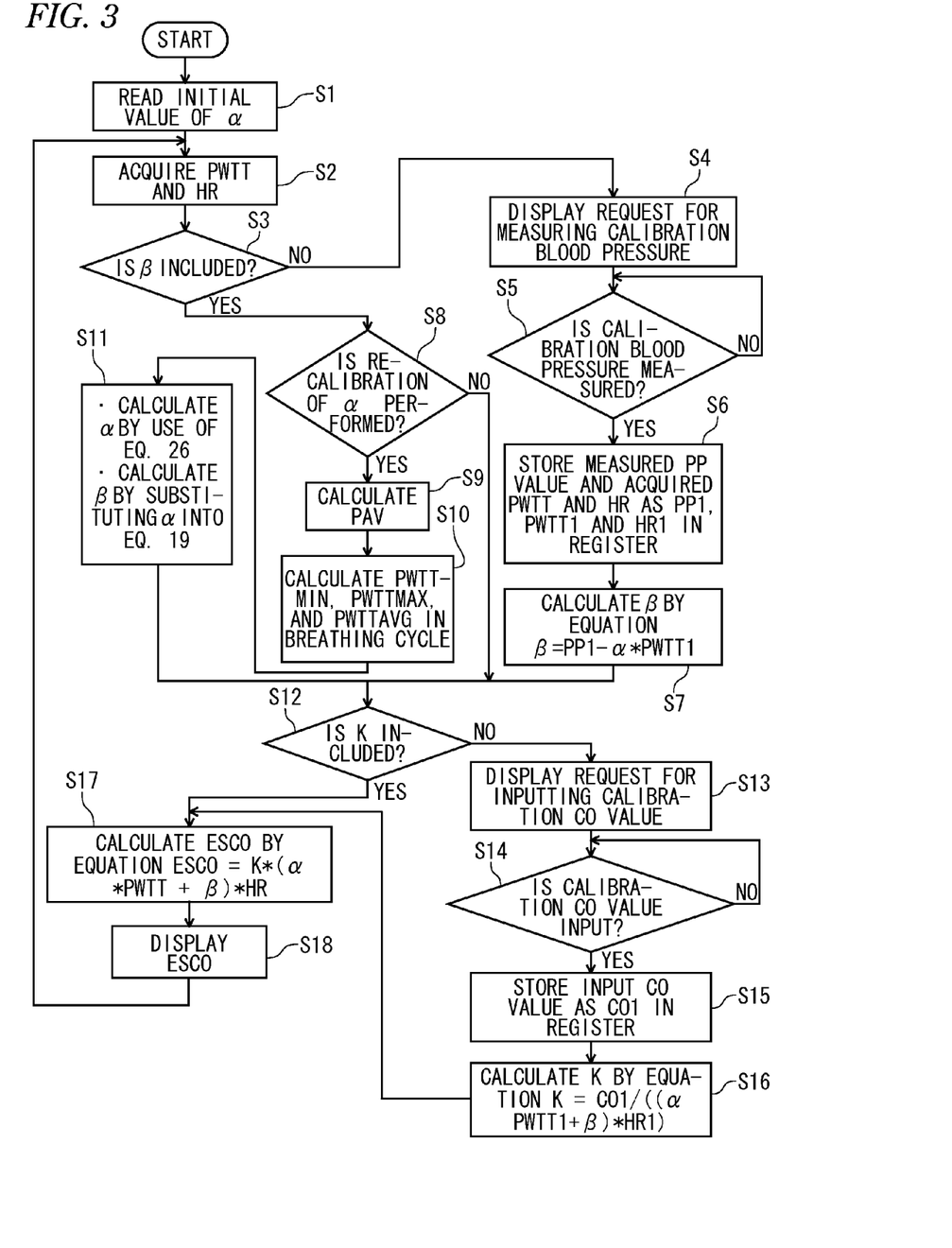
FIG. 3 is a flowchart illustrating procedures for computing esCO by calibration of $\alpha$, $\beta$, and K.

An initial value of the coefficient $\alpha$ is first read (step S1). Subsequently, PWTT and HR are acquired by actual measurement (step S2). The acquired PWTT is a value from which respiratory variations are eliminated. Further, the HR (heart rate) is calculated and acquired from the R wave in the electrocardiogram measured by the time interval detection reference point measurement unit 31.

Step S3 determines whether or not there is the coefficient $\beta$. The factors $\alpha$ and $\beta$ are coefficients inherent in the patient to be experimentally determined. If the coefficient β is determined not to be included in step S3 (No in step S3), a request message for measuring calibration blood pressure is displayed on the display section 62 (step S4).

Subsequently, Step S5 determines whether or not the calibration blood pressure is measured. If the blood pressure is not measured (No in step S5), processing waits until measurement is carried out. In contrast, If the blood pressure is measured (Yes in step S5), a PP value, which has been measured on the basis of the blood pressure value, and the acquired PWTT and HR are stored as PP1, PWTT1, and HR1 in a register (step S6).

The stored values and the initial value α read in step S1 are subsequently substituted into Equation β=PP1−α*PWTT1, thereby calculating the coefficient β (step S7). The equation is derived from SV=K*PP (Eq. 4) and SV=K*(α*PWTT+*β) (Eq. 14).

Processing proceeds to step S12 after calculation of the coefficient β, and step S12 determines whether or not the coefficient K is included.

In the meantime, if the coefficient β is determined to be included in step S3 (Yes in step S3), step S8 determines whether or not the initial value α read in step S1 is re-calibrated. If in step S8, it is determined that re-calibration of the coefficient α is not performed, processing proceeds to step S12, where step S12 determines whether or not the coefficient K is included.

If in step S8, it is determined that re-calibration of the coefficient α is performed, PAV, which represents respiratory variations in an amplitude of a pulse wave measured by a pulse oximeter, is calculated as follows (step S9):

The following relationships exist among the coefficients K, α, and β.

SV=K*PP (Eq. 4) and SV=CO/HR give $$K=CO1/(PP1*HR1) \quad (Eq. 17).$$

SV=K*PP (Eq. 4) and SV=K*(α*PWTT+β) (Eq. 14) give $$PP1=\alpha PWTT1+\beta \quad (Eq. 18).$$

$$\text{Therefore, } \beta=PP1-\alpha PWTT1 \quad (Eq. 19),$$

where PP1, PWTT1, and HR1 are values of the factors PP, PWTT, and HR actually measured during calibration. These measured values are those from which respiratory values are eliminated.

Let the minimum value and the maximum value of PWTT in a respiratory cycle measured by the PWTT respiratory variation measurement unit 14 be taken as PWTTmin and PWTTmax, the maximum value SVmax and the minimum value SVmin of SV in a respiratory cycle calculated by the patient's inherent coefficient calculation unit 18 are determined as follows:

$$SV\text{max}=K(\alpha PWTT\text{min}+\beta) \quad (Eq. 20)$$

$$SV\text{min}=K(\alpha PWTT\text{max}+\beta) \quad (Eq. 21)$$

An average value of SV in a respiratory cycle is determined as follows:

[Mathematical Expression 1]
$$SVavg = \frac{1}{n}\sum_{i=1}^{n} K(\alpha PWTTi + \beta)$$

$$SVavg = K(\alpha PWTTavg + \beta) \quad (Eq. 22)$$

Therefore, SVV that designates respiratory variations in SV are determined by Eq. 20, Eq. 21, and Eq. 22 as follows:

$$SVV = (SV\text{max} - SV\text{min})/SVavg \quad (Eq. 23)$$

$$= K(\alpha PWTT\text{min}+\beta - \alpha PWTT\text{max}-\beta)/K(\alpha PWTTavg+\beta)$$

$$= K\alpha(PWTT\text{min}-PWTT\text{max})/K(\alpha PWTTavg+\beta)$$

$$= (PWTT\text{min}-PWTT\text{max})/(PWTTavg+\beta/\alpha)$$

The respiratory variations in an amplitude of a pulse wave PAV having an oximetry waveform can be calculated as follows.

$$PAV=(Amp\text{max}-Amp\text{min})/Ampavg \quad (Eq. 24)$$

Let SVV be tantamount to PAV, Eq. 23 and Eq. 24 will give $$PAV=(PWTT\text{min}-PWTT\text{max})/(PWTTavg+\beta/\alpha) \quad (Eq. 25).$$

Subsequently, the minimum value of PWTT: PWTTmin, the maximum value: PWTTmax, and the average value: PWTTavg are then calculated (step S10).

β=PP1−αPWTT1 (Eq. 19) is substituted into Eq. 25, thereby giving

PAV*(αPWTTavg+PP1−αPWTT1)=α(PWTTmin−PWTTmax).

From α*(PAV*PWTTavg−PAV*PWTT1+PWTTmax−PWTTmin)=−PAV*PP1, the coefficient α is calculated as follows:

$$\alpha = -(PAV*PP1)/(PAV*(PWTTavg-PWTT1)+ \\ PWTT\text{max}-PWTT\text{min}) \quad (Eq. 26)$$

In addition, the coefficient β can be calculated by substituting the coefficient α into β=PP1−αPWTT1 (Eq. 19) (step S11).

If NO is given as a determination in step S8, after processing pertinent to step S7 and step S11, step S12 determines whether the coefficient K is included.

If the coefficient K is determined not to be included in step S12 (No in step S12), a request for inputting a calibration CO value is displayed on the display section 62 (step S13). Subsequently, step S14 determines whether or not the calibration CO value is input (step S14). If the CO value is not input (No in step S14), processing waits until the CO value is input. In contrast, If the CO value is input (Yes in step S14), the input CO value is stored as CO1 in the register (step S15).

Subsequently, the stored CO1 value and the calculated coefficients α, β, PWTT1, and HR1 are substituted into K=CO1/((α*PWTT1+β)*HR1), thereby calculating the coefficient K (step S16). The equation is derived from K=CO1/(PP1*HR1) (Eq. 17) and PP1=αPWTT1+β (Eq. 18).

The coefficients α, β, and K determined by calibration are substituted into the equation esCO=K*(α*PWTT+β)*HR, thereby calculating esCO (step S17). Even if the coefficient K is determined to be included in step S12 (Yes in step S12), processing proceeds to step S17, thereby calculating esCO.

The calculated esCO is displayed in the display section 62 (step S18).

Subsequently, processing returns to step S2, where foregoing processing is continuously iterated.

In step S9, the PPV (respiratory variations in pulse pressure of a patient) measured by the pulse pressure respiratory variation measurement unit 52 can also be used in place of the PAV (respiratory variations in an amplitude of a pulse wave).

As above, according to the blood volume measurement method and the measurement apparatus of the embodiment, the coefficients α, β, and K can be calibrated by only single blood pressure measurement with use of at least two types of parameters of respiratory variations. Therefore, there can be obviated a necessity for measuring blood pressure twice while changing calibration blood pressure, which has hitherto been practiced in the related art. Therefore, measurement of a blood volume can be simplified, and a blood volume can be calculated without imposing stress on the patient.

Since the respiratory variations in stroke volume (SVV), respiratory variations in an amplitude of a pulse wave (PAV), and respiratory variations in pulse pressure (PPV) are used as respiratory variation parameters, the measurement method can be simplified further, so that an inspection time can be shortened.

While the embodiment(s) of the presently disclosed subject matter has(have) been illustrated and described, it will be appreciated that various changes can be made therein without departing from the spirit and scope of the presently disclosed subject matter.

For instance, the embodiment has mentioned the example in which the CO value, which is a cardiac output per unit time (e.g., one minute), is used in steps S13 to S16. However, the presently disclosed subject matter is not limited to the example. A volume of blood flowed into the aorta during the systole of the heart; in other words, SV that is a stroke volume, can also be used. To be more specific, if the coefficient K is determined not to be included in step S12 (No in step S12), a request for inputting a calibration SV value is displayed on the display 62 (step S'13). Subsequently, step S'14 determines whether or not the calibration SV value is input. If the calibration SV value is not input (No in step S'14), processing waits until the calibration SV value is input. In contrast, if the SV value is input (Yes in step S'14), the input SV value is stored as SV1 in the register (step S'15).

The stored SV1 value and the calculated coefficients α, β, PWTT1, and HR1 are substituted into the equation K=SV1/(α*PWTT1+β), thereby calculating the coefficient K (step S'16). Even in such a modified example, the apparatus operates in the same manner as the above-described embodiment. Therefore, measuring a blood volume is not time-consuming, and method for measuring a blood volume is simple, so that stress exerted on the patient, which will be imposed by measurement, can be assuaged.

The blood volume measurement method and the blood volume measurement apparatus of the presently disclosed subject matter can enable measurement of a blood volume by only single measurement of blood pressure. Hence, measurement of a blood volume doesn't require a time-consuming, and stress on a patient which will be imposed by measurement can be assuaged.

What is claimed is:

1. A blood volume measurement method for calculating a cardiac output (CO) from a pulse wave transit time, the method comprising the steps of:
   measuring respiratory variations of at least two types of parameters;
   measuring a pulse wave transit time (PWTT) in a respiratory cycle;
   measuring a heart rate (HR) in a predetermined time; and
   calculating and outputting, by a computer, a cardiac output (CO) by use of the respiratory variations of at least the two types of parameters, the pulse wave transit time, and the heart rate; and
   wherein patient's inherent coefficients α, β, and K are calculated by use of the respiratory variations of at least the two types of parameters and the pulse wave transit time, and the cardiac output is determined by an equation $CO = K(\alpha * PWTT + \beta) * HR$; and wherein the patient's inherent coefficient α is determined by an equation $\alpha = -(PAV * PP1)/(PAV*(PWTTavg - PWTT1) + PWTTmax - PWTTmin)$, where PAV is an amplitude of a pulse wave; PP1 is actually measured pulse pressure; PWTTavg is an average pulse wave transit time in a respiratory cycle; PWTT1 is an actually measured pulse wave transit time; PWTTmax is a maximum value of pulse wave transit time in the respiratory cycle; and PWTTmin is a minimum value of pulse wave transit time in the respiratory cycle.

2. The blood volume measurement method according to claim 1, wherein the respiratory variations of at least the two types of parameters comprise respiratory variations in stroke volume (SVV) and respiratory variations in an amplitude of a pulse wave (PAV).

3. The blood volume measurement method according to claim 1, wherein the respiratory variations of at least the two types of parameters comprise respiratory variations in stroke volume (SVV) and respiratory variations in pulse pressure (PPV).

4. A blood volume measurement apparatus that calculates a cardiac output (CO) from a pulse wave transit time, comprising:
   a processor configured to:
   determine respiratory variations of at least two types of parameters;
   detect a pulse wave transit time (PWTT) in a respiratory cycle;
   calculate a heart rate (HR) in a predetermined time; and
   calculate and output a cardiac output (CO) with use of the respiratory variations of at least the two types of parameters, the pulse wave transit time, and the heart rate; and
   wherein patient's inherent coefficients α, β, and K are calculated by use of the respiratory variations of at least the two types of parameters and the pulse wave transit time, and the cardiac output is determined by an equation $CO = K(\alpha * PWTT + \beta) * HR$; and wherein the patient's inherent coefficient α is determined by an equation $\alpha = -(PAV * PP1)/(PAV*(PWTTavg - PWTT1) + PWTTmax - PWTTmin)$, where PAV is an amplitude of a pulse wave; PP1 is actually measured pulse pressure; PWTTavg is an average pulse wave transit time in a respiratory cycle; PWTT1 is an actually measured pulse wave transit time; PWTTmax is a maximum value of pulse wave transit time in the respiratory cycle; and PWTTmin is a minimum value of pulse wave transit time in the respiratory cycle.

5. The blood volume measurement method according to claim 4, wherein the respiratory variations of at least the two types of parameters comprise respiratory variations in stroke volume (SVV) and respiratory variations in an amplitude of a pulse wave (PAV).

6. The blood volume measurement method according to claim 4, wherein the respiratory variations of at least the two types of parameters comprise respiratory variations in stroke volume (SVV) and respiratory variations in pulse pressure (PPV).

\* \* \* \* \*